US00PP30720P2

(12) United States Plant Patent
Flore

(10) Patent No.: US PP30,720 P2
(45) Date of Patent: Jul. 16, 2019

(54) ***PHALAENOPSIS* PLANT NAMED 'MI00690'**

(50) Latin Name: *Phalaenopsis hybrida*
Varietal Denomination: MI00690

(71) Applicant: Febe Flore, Lochristi (BE)

(72) Inventor: Febe Flore, Lochristi (BE)

(73) Assignee: Floreac N.V. div. Microflor, Lochristi (BE)

( * ) Notice: Subject to any disclaimer, the term of this patent is extended or adjusted under 35 U.S.C. 154(b) by 0 days.

(21) Appl. No.: 15/732,945

(22) Filed: Jan. 12, 2018

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Phalaenopsis* plant named 'MI00690', characterized by its relatively compact and upright plant habit; moderately vigorous growth habit; strong flowering stems; freely flowering habit with typically three racemes per plant, each inflorescence with numerous flowers; and showy purple-colored flowers densely covered with large red purple-colored spots.

2 Drawing Sheets

Botanical designation: *Phalaenopsis hybrida.*
Cultivar denomination: 'MI00690'.

BACKGROUND OF THE INVENTION

The present invention relates to a new and distinct cultivar of *Phalaenopsis* plant, botanically known as *Phalaenopsis hybrida*, and hereinafter referred to by the name 'MI00690'.

The new *Phalaenopsis* plant is a product of a planned breeding program conducted by the Inventor in Lochristi, Belgium. The objective of the breeding program is to develop new freely flowering *Phalaenopsis* plants with good leaf shape and unique and attractive flower patterns and coloration.

The new *Phalaenopsis* plant originated from a cross-pollination in March, 2009 in Lochristi, Belgium of a proprietary selection of *Phalaenopsis hybrida* identified as code number PHM00007, not patented, as the female, or seed, parent with a proprietary selection of *Phalaenopsis hybrida* identified as code number PHM00093, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in May, 2012.

Asexual reproduction of the new *Phalaenopsis* plant by in vitro meristem propagation in a controlled environment in Lochristi, Belgium since November, 2013 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI00690'. These characteristics in combination distinguish 'MI00690' as a new and distinct *Phalaenopsis* plant:

1. Relatively compact and upright plant habit.
2. Moderately vigorous growth habit.
3. Strong flowering stems.
4. Freely flowering habit with typically three racemes per plant, each inflorescence with numerous flowers.
5. Showy purple-colored flowers densely covered with large red purple-colored spots.

Plants of the new *Phalaenopsis* can be compared to plants of the female parent selection. Plants of the new *Phalaenopsis* differ primarily from plants of the female parent selection in flower color as flowers of the female parent selection are blush white in color. In addition, plants of the new *Phalaenopsis* have larger flowers than plants of the female parent selection.

Plants of the new *Phalaenopsis* can be compared to plants of the male parent selection. Plants of the new *Phalaenopsis* differ primarily from plants of the male parent selection in flower color as plants of the male parent selection are velvety red in color. In addition, plants of the new *Phalaenopsis* are shorter and have smaller flowers than plants of the male parent selection.

Plants of the new *Phalaenopsis* can be compared to plants of *Phalaenopsis hybrida* 'CX297', not patented. In side-by-side comparisons, plants of the new *Phalaenopsis* differ primarily from plants of 'CX297' in flower color as flowers of the new *Phalaenopsis* have white-colored labellum whereas plants of 'CX297' have red-colored labellum. In addition, plants of the new *Phalaenopsis* have thinner and more flexible spikes than plants of 'CX297'.

Plants of the new *Phalaenopsis* can also be compared to plants of *Phalaenopsis hybrida* 'CX322', not patented. In side-by-side comparisons, plants of the new *Phalaenopsis* differ primarily from plants of 'CX322' in flower color as flowers of the new *Phalaenopsis* have white-colored labellum whereas plants of 'CX322' have red-colored labellum. In addition, plants of the new *Phalaenopsis* have thinner and more flexible spikes than plants of 'CX322'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet is a side perspective view of a typical flowering plant of 'MI00690' grown in a container.

The photograph at the top of second sheet is a close-up view of a typical flower of 'MI00690'.

DETAILED BOTANICAL DESCRIPTION

The aforementioned photographs and following observations and measurements describe plants grown during the autumn and early winter in 9-cm containers in a glass-covered greenhouse in Lochristi, Belgium and under cultural practices typically used in commercial *Phalaenopsis* production. During the production of the plants, day and night temperatures ranged from 18° C. to 29° C. and light levels ranged from 150 Watt/m$^2$ to 375 Watt/m$^2$. Plants were 76 weeks old when the photographs and description were taken. In the following description, color references are made to The Royal Horticultural Society Colour Chart, 2015 Edition, except where general terms of ordinary dictionary significance are used.

Botanical classification: *Phalaenopsis hybrida* 'MI00690'.

Parentage:

- *Female parent*.—Proprietary selection of *Phalaenopsis hybrida* identified as code number PHM00007, not patented.
- *Male parent*.—Proprietary selection of *Phalaenopsis hybrida* identified as code number PHM00093, not patented.

Propagation:

- *Type*.—By in vitro meristem propagation.
- *Time to initiate roots, summer*.—About nine to ten weeks at temperatures about 26° C.
- *Time to initiate roots, winter*.—About ten to eleven weeks at temperatures about 26° C.
- *Time to produce a rooted young plant, summer*.—About 140 to 160 days at temperatures about 26° C.
- *Time to produce a rooted young plant, winter*.—About 150 to 180 days at temperatures about 26° C.
- *Root description*.—Thick, fleshy; typically grey green in color, towards the apex, close to light green; actual color of the roots is dependent on substrate composition, water quality, fertilizer, substrate temperature and age of roots.
- *Rooting habit*.—Low to non-branching; sparse.

Plant description:

- *Plant form and growth habit*.—Herbaceous epiphyte; upright plant habit with typically three branched racemes per plant, each inflorescence with numerous flowers; monopodial; moderately vigorous growth habit and moderate growth rate.
- *Plant height, substrate level to top of foliar plane*.—About 11.4 cm.
- *Plant height, substrate level to top of inflorescences*.—About 32 cm.
- *Plant diameter or spread*.—About 32.8 cm.

Leaf description:

- *Arrangement and quantity*.—Distichous, simple; sessile; about eight per plant.
- *Length*.—About 13.4 cm.
- *Width*.—About 6.1 cm.
- *Aspect*.—Mostly flat to arching.
- *Shape*.—Obovate to elliptical; slightly carinate.
- *Apex*.—Broadly acute, unequal.
- *Base*.—Sheathing.
- *Margin*.—Entire; slightly revolute to non-revolute.
- *Texture and luster, upper surface*.—Smooth, glabrous; slightly to moderately glossy.
- *Texture and luster, lower surface*.—Slightly furrowed, glabrous; slightly glossy.
- *Venation pattern*.—Camptodromous.
- *Color*.—Developing leaves, upper surface: Close to NN137A. Developing leaves, lower surface: Close to between 146A and 147B. Fully expanded leaves, upper surface: Close to slightly darker NN137A; venation, close to slightly darker than NN137A. Fully expanded leaves, lower surface: Close to 146A; venation, close to 143A.

Inflorescence description:

- *Appearance and flowering habit*.—Showy zygomorphic flowers arranged on axillary branched racemes; typically three racemes per plant; each inflorescence with about nine flowers; flowers face outwardly on arching inflorescences supported by upright peduncles; flowers with three petals, two lateral petals and one center petal transformed into a labellum and three sepals.
- *Fragrance*.—None detected.
- *Time to flower*.—Plants begin flowering about 18 weeks after an inductive cooling period.
- *Flower longevity*.—Long flowering period, individual flowers maintain good substance for about five months on the plant; flowers not persistent.
- *Inflorescence length* (*lowermost flower to inflorescence apex*).—About 15.5 cm.
- *Inflorescence width*.—About 14.8 cm.
- *Flower buds*.—Height: About 1.8 cm. Diameter: About 1.2 cm. Shape: Broadly ovate. Color: Close to between 146D and 147C; irregularly striped and flushed with close to 183A to 183B.
- *Flower diameter*.—About 5.1 cm by 5.5 cm.
- *Flower depth*.—About 4.6 cm.
- *Petals, quantity and arrangement*.—Three, two lateral petals and one center petal transformed into a labellum.
- *Lateral petals*.—Length: About 2.8 cm. Width: About 3.1 cm. Shape: Reniform. Apex: Rounded. Margin: Entire. Texture and luster, upper and lower surfaces: Smooth, glabrous, velvety; matte. Color: When opening, upper surface: Close to N78C and N78D slightly flushed with close to N78B; towards the margins, close to N155A; proximal 66% of petal is densely dotted and flushed with slightly darker than 71A; at the base, close to N78B to N78C. When opening, lower surface: Close to N78D and N80D; slightly dotted with close to NN78C. Fully opened, upper surface: Close to N78C and N78D; towards the margins, close to N155A; proximal 66% of petal is densely dotted and flushed with slightly darker than 71A; at the base, close to N78C; color does not change with development. Fully opened, lower surface: Close to N78D and N80D; slightly dotted with close to NN78C; color does not change with development.

*Labellum*.—Appearance: Tri-lobed with two lateral lobes and a central lobe. Length, lateral lobe: About 1.6 cm. Width, lateral lobes: About 1.2 cm. Length, central lobe: About 2.6 cm. Width, central lobe: About 1.7 cm. Shape, lateral lobes: Obovate. Shape, central lobe: Roughly deltoid. Apex, lateral lobes: Obtuse. Apex, central lobe: Cleft with two moderately long narrow recurved cirrose tips. Margins, lateral lobes: Entire, undulate. Margins, central lobe: Entire. Texture and luster, upper and lower surfaces: Glabrous, velvety; matte. Callosities: Located at the base of the labellum and attachment point of the lateral petals; about 4 mm in length, about 4 mm in width and about 3 mm in height. Color: When opening, upper surface: Lateral lobes: Close to NN155D; towards the base, close to 59A; basal margins, close to 8C. Central lobe: Close to 76C tinged with close to 26D; basal margins, close to N78D; cirrose apices, close to 76D. Callosities: Close to between N186C and 200A to 200B; margins, close to 16D. When opening, lower surface: Lateral lobes: Close to NN155D; towards the base, tinged with close to 186D; basal margins, close to 9D. Central lobe: Close to 76C; main vein, close to N78C to N78D; basal margins, close to 77C; cirrose apices, close to 76D. Fully opened, upper surface: Lateral lobes: Close to NN155D; towards the base, close to 59A; basal margins, close to 4C to 4D. Central lobe: Close to 76C to 76D; towards the margins, close to NN155D tinged with close to 16D; basal margins, close to N78D; cirrose apices, close to NN155D. Callosities: Close to between N186C and 200A to 200B; margins, close to 16D. Fully opened, lower surface: Lateral lobes: Close to NN155D; towards the base, tinged with close to 186C to 186D; basal margins, close to 9D. Central lobe: Close to 76C to 76D; basal margins, close to 77C; cirrose apices, close to NN155D.

*Sepals*.—Quantity and arrangement: Three, two lower lateral sepals and one upper dorsal sepal. Length, lateral and dorsal sepals: About 3 cm. Width, lateral sepals: About 1.8 cm. Width, dorsal sepal: About 2.1 cm. Shape, lateral and dorsal sepals: Ovate. Apex, lateral sepals: Broadly and bluntly acute. Apex, dorsal sepal: Obtuse. Base, lateral and dorsal sepals: Truncate. Margin, lateral and dorsal sepals: Entire. Texture and luster, lateral and dorsal sepals, upper and lower surfaces: Smooth, glabrous, velvety; matte. Color, lateral sepals: When opening, upper surface: Close to NN155A; towards the base, close to 157B; towards the apex, close to 77B to 77C; apical margins, close to N155A; densely dotted and flushed with close to 59A, 71A and between 59A to 71A. When opening, lower surface: Close to 76C; towards the apex and margins, close to 77C; towards the base, close to N148C; dots, close to 77B. Fully opened, upper surface: Close to NN155A; towards the base, close to 157B; towards the apex, close to 77B to 77C; apical margins, close to N155A; densely dotted and flushed with close to 59A, 71A and between 59A to 71A. Fully opened, lower surface: Close to 76C; towards the apex and margins, close to 77C; towards the base, close to N148C; dots, close to 77B. Color, dorsal sepal: When opening, upper surface: Close to 77C; margins, close to N155A; densely dotted and flushed with between and darker than 59A to 71A. When opening, lower surface: Close to 76C; towards the apex and margins, close to 77C; towards the base, close to N148C; dots, close to 77B. Fully opened, upper surface: Close to 77B; margins, close to N155A; densely dotted and flushed with between and darker than 59A to 71A. Fully opened, lower surface: Close to 76C; towards the apex and margins, close to 77C; towards the base, close to N148C; dots, close to 77B.

*Peduncles*.—Length: About 32.5 cm. Diameter: About 3.5 mm. Strength: Very strong. Aspect: Upright to about 35° from vertical. Texture and luster: Smooth, glabrous; matte. Color: Close to 137B.

*Pedicels*.—Length: About 2.3 cm. Diameter: About 2 mm. Strength: Moderately strong. Aspect: About 70° from peduncle axis. Texture and luster: Smooth, glabrous; matte. Color: Close to 146C; distally, close to 150D; proximally, close to 200A.

*Reproductive organs*.—Androecium: Column length: About 6 mm. Column width: About 4 mm. Column color: Close to 77B. Pollinia quantity: Two. Pollinia diameter (per two pollinia): About 2 mm. Pollinia color: Close to 23A. Gynoecium: Stigma length: About 3 mm. Stigma width: About 3 mm. Stigma shape: Reniform. Stigma color: Close to N155A. Ovary length: About 4 mm. Ovary diameter: About 1.5 mm. Ovary color: Close to lighter than 145D. Seeds and fruits: Seed and fruit development have not been observed on plants of the new *Phalaenopsis* to date.

Pathogen & pest resistance: Plants of the new *Phalaenopsis* have not been shown to be resistant to pathogens and pests common to *Phalaenopsis* plants.

Temperature tolerance: Plants of the new *Phalaenopsis* have been observed to tolerate high temperatures of about 40° C. and suitable for USDA Hardiness Zone 10.

It is claimed:

1. A new and distinct *Phalaenopsis* plant named 'MI00690' as illustrated and described.

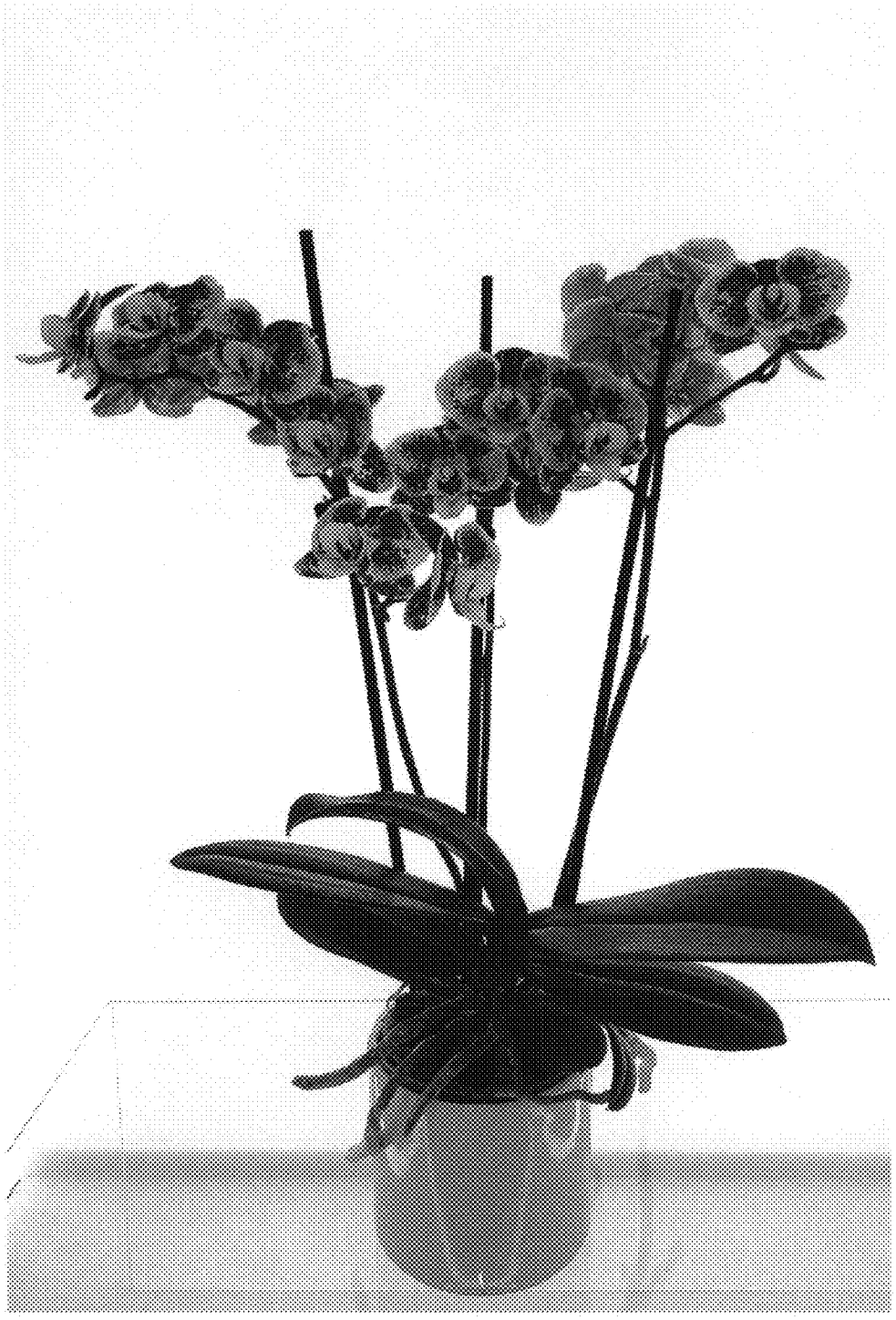

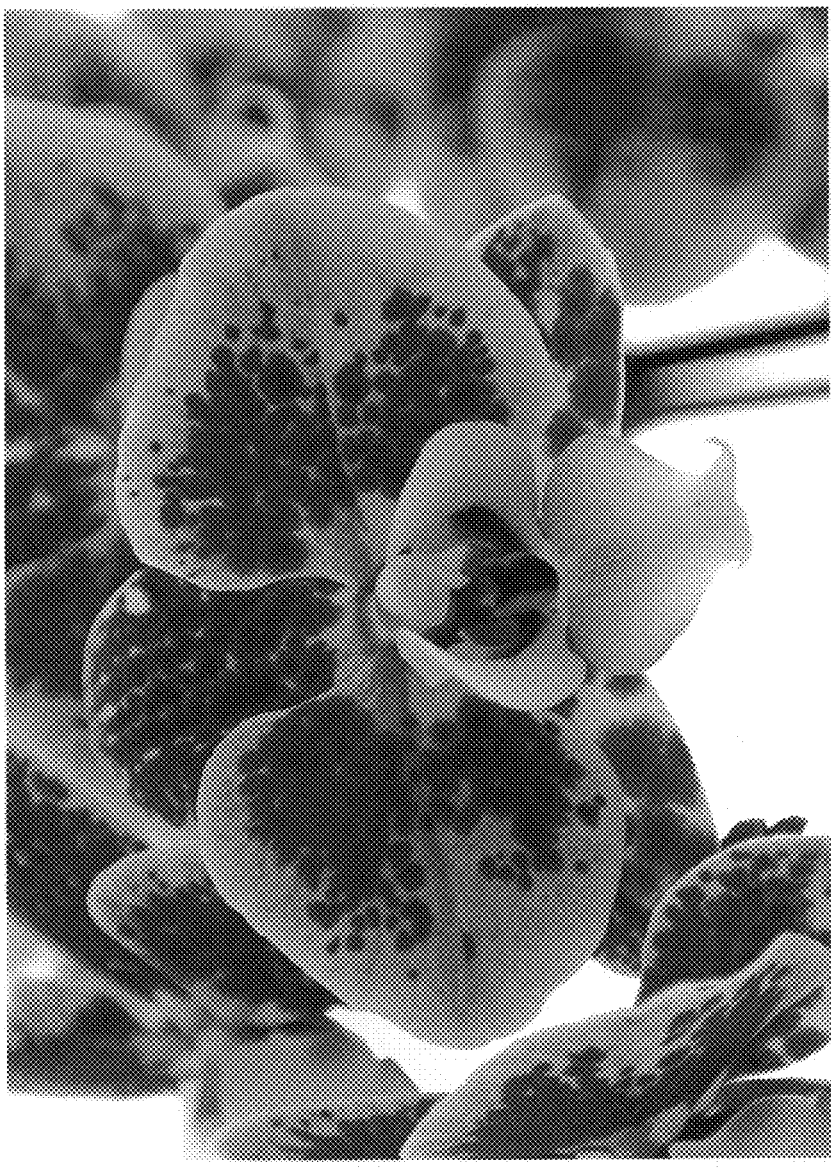

* * * * *